United States Patent [19]

Hasseberg et al.

[11] Patent Number: 5,672,745
[45] Date of Patent: Sep. 30, 1997

[54] METHOD FOR THE CONTINUOUS PREPARATION OF METHIONINE OR METHIONINE DERIVATIVES

[75] Inventors: Hans-Albrecht Hasseberg, Rodenbach; Klaus Huthmacher, Gelnhausen; Stephan Rautenberg; Heinrich Petsch, both of Hanau; Horst Weigel, Rodenbach, all of Germany

[73] Assignee: Degussa Aktiengesellschaft, Frankfurt am Main 1, Germany

[21] Appl. No.: 416,900

[22] PCT Filed: Oct. 14, 1993

[86] PCT No.: PCT/EP93/02838

§ 371 Date: May 23, 1995

§ 102(e) Date: May 23, 1995

[87] PCT Pub. No.: WO94/08957

PCT Pub. Date: Apr. 28, 1994

[30] Foreign Application Priority Data

Oct. 20, 1992 [DE] Germany .................. 42 35 295.9

[51] Int. Cl.$^6$ .................................................. C07C 321/00
[52] U.S. Cl. ................................. 562/559; 562/575
[58] Field of Search ............................ 562/575, 559

[56] References Cited

U.S. PATENT DOCUMENTS

| | | | |
|---|---|---|---|
| 4,243,814 | 1/1981 | Pascal | 562/575 |
| 4,459,423 | 7/1984 | Doya | 562/575 |
| 4,677,224 | 6/1987 | Commeyras | 562/575 |
| 4,851,576 | 7/1989 | Commeyras | 562/575 |
| 4,960,932 | 10/1990 | Gillonnier | 562/559 |

FOREIGN PATENT DOCUMENTS

| | | | |
|---|---|---|---|
| 84470 | 7/1983 | European Pat. Off. | |
| 228938 | 7/1987 | European Pat. Off. | 562/559 |
| 2405924 | 5/1979 | France . | |

*Primary Examiner*—Michael L. Shippen
*Attorney, Agent, or Firm*—Cushman Darby & Cushman, IP Group of Pillsbury Madison & Sutro, L.L.P.

[57] ABSTRACT

The direct saponification of methionine nitrile obtained from methylmercaptopropionaldehyde, prussic acid and ammonia gives low yields, catalyst and educt losses and unwanted side-products. The aim of the invention is therefore to provide a method which can be carried out without isolating the intermediate products, in particular continuously, and with low losses. The ketone used is recovered in high yields after amide saponification since this liberates the ketone from side-products. In order to recover the ammonia, it is necessary for the ammonia to be substantially freed of ketone, the mixture of ammonia, ketone and water obtained being separated under pressure in a separation column. When the amide is saponified at $\geq 160°$ C., amide concentrations of less than 25% by wt. are preferred. Methionine nitrile is produced by treatment with at least 4 equivalents of $\geq 50\%$ by wt. ammonia at between 40° and 80° C./or between 5 and 60 min. Cyanide residues are destroyed by heating to over 150° C. Methionine is of particular use as a feedstuff, in particular in aqueous solution.

18 Claims, 1 Drawing Sheet

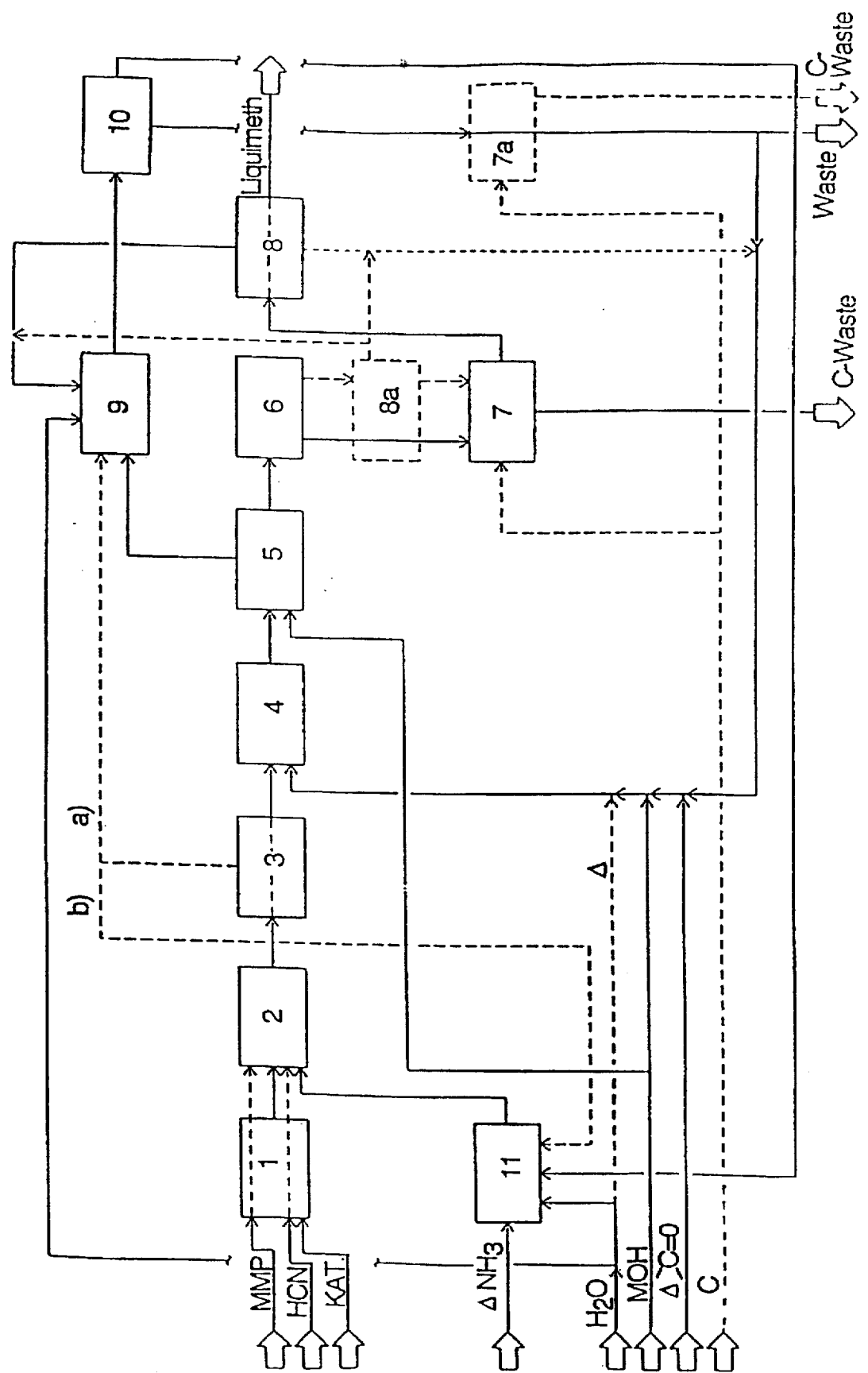

METHOD FOR THE CONTINUOUS PREPARATION OF METHIONINE OR METHIONINE DERIVATIVES

The present invention relates to a process, which may preferably be performed continuously, suitable for the large-scale industrial production of aqueous alkali metal or alkaline earth metal methioninate solutions which may be used directly, for example as feed additives, or for the isolation of amino acid or salts thereof suitable for use as feed additives. The process is suitable in particular for the production of methioninate solution. Methionine and aqueous solutions of methionine salts, in particular of sodium methioninate (DE 31 05 009 C), together with substitutes such as methionine hydroxy analogue (MHA) are used world-wide as feed additives for rearing poultry, pigs and other agro-economic animals and are mainly useful for the production of animal proteins. It is particularly in view of the increasing world population and increasing problems of food supply that methionine, being one of the essential amino acids in the animal growth process, and its various forms are of special importance and so too, consequently, is the more economic production thereof. Depending upon requirements, the products are preferably used in solid or liquid form.

Commercially available sodium methioninate solution has a concentration of 40 wt. % of methionine and, unlike the substitute, MHA, it has equivalent biological value to solid methionine, measured on an equimolar basis. There are three main methods available for the production of such sodium methioninate solutions:

1. Simple dissolution of isolated methionine.

Although this method produces the purest form of the product, it is more expensive than production of the solid form due to the additional processing stage and is thus less economical than the production of methionine itself.

2. Alkaline hydrolysis of 5-(β-methylmercaptoethyl) hydantoin with NaOH or NaOH/Ca(OH)$_2$ mixtures for which it is necessary to use approximately 2-3 hydroxy equivalents to avoid the production of unwanted by-products.

When Ca(OH)$_2$ is used, while the excess saponification agent may be removed in the form of calcium carbonate (DE 31 05 006 C), it must however be disposed of as virtually unusable waste salt or returned to the hydroxide form, in which it may be reused but which requires expensive steps such as calcining and quenching. On the other hand, when sodium hydroxide solution is used alone, the excess must either be removed in the form of the sodium carbonate produced (DE 31 04 997 A) or it must be removed as sodium sulphate which is formed after neutralisation of the sodium carbonate with sulphuric acid (EP 253 740). Salt formation and the expensive salt removal process as well as the risk of undesirable residues being left behind in the product solution constitute the disadvantages of this method.

3. Alkaline hydrolysis of methionine amide

As is known, for example from EP 0 228 938, this may be performed with approximately stoichiometric quantities of hydroxide without giving rise to excessive by-product formation. This constitutes an important advantage in comparison with method 2.

Methionine amide may be prepared in a known manner by hydrolysing methionine nitrile, which may in turn be obtained by direct synthesis from the customary starting materials, methylmercaptopropionaldehyde (MMP), hydrocyanic acid or ammonium cyanide, and ammonia.

The method of acid-catalysed nitrile hydrolysis cannot be used as it inevitably leads to the formation of neutral salt, while alkaline nitrile hydrolysis is preferably performed with the addition of catalytically active carbonyl compounds, in particular ketones (Houben-Weyl, *Methoden der Organischen Chemie*, enlarged supplementary volumes to the 4th edition, volume E5, pages 535 et seq., and the literature cited therein).

As considerable expense and losses are entailed in isolating methionine cleanly and subsequently hydrolysing it to NaMet with NaOH as described, for example, in patent EP 228 938, such a process is uneconomic.

In the other example stated in the same patent, MMP-cyanohydrin is first prepared in the customary manner from MMP and HCN in a 500 ml pressure vessel, and the MMP-cyanohydrin is then converted into methionine nitrile by the introduction of condensed NH$_3$. After release of pressure and cooling from 60° C. to 10° C., this product (see Houben-Weyl) is reacted with an aqueous solution of acetone and NaOH, and any remaining ammonia and acetone are then removed by the application of a vacuum before the resultant methionine amide is hydrolysed to sodium methioninate after the addition of sodium hydroxide solution at 180° C. Subsequent release of pressure and removal of residual ammonia under vacuum results in a solution of sodium methioninate which, in addition to methionine, still contains at least 10 other by-products in varying but not negligible concentrations. This laboratory method is unsuitable for customary large-scale industrial production of several tens of thousands of tonnes per year of methionine per plant. Moreover, no statement is made concerning the residues of acetone and the possibility of recycling it, nor about the possibilities of recycling the large excess of NH$_3$ introduced into the process. Apart from the optimum arrangement of the desired synthetic pathway with regard to yield and selectivity, the completest possible recovery of the ammonia used in excess and of the necessary ketone catalyst in a recyclable form and subsequent reuse of both are, however, preconditions for an economic process which should, moreover, be capable of being performed continuously on the desired scale.

No continuous process for a homogeneous ketone-catalysed alkaline aminonitrile hydrolysis has hitherto been described. The reason for this is apparently that no effective industrial method which may be performed continuously for purifying the resulting mixture of ketone, ammonia, water and optionally by-products has hitherto been available.

The importance of this problem is evident from the fact that catalytically active polymer resins containing carbonyl groups have been developed as ketone substitutes (EP 84 470, DD 208 349), which may readily be removed from the reaction medium by filtration or which may be arranged as a fixed bed through which the substrate solution may be passed continuously.

This at first sight very attractive concept has, however, the disadvantage that such catalysts have not hitherto been commercially available and would presumably be very expensive to produce in the quantities required for large-scale industrial production, in contrast to ketones, which are inexpensive. Moreover, the polymer resins described are rapidly poisoned by secondary reactions on the carbonyl groups and must be regenerated by expensive processes.

In a variation of this process (EP 168 282, U.S. Pat. No. 4,677,224), an increase in catalyst life is achieved at the expense of substantial re-dilution of the aminonitrile solution used for hydrolysis from approximately 1M to 0.1M by the product solution produced in the subsequent saponification stage.

This is also disadvantageous for large-scale industrial production. Firstly, it requires the use of correspondingly larger columns filled with polymer catalyst, at least two of which are required, wherein it is nonetheless still not possible completely to dispense with catalyst regeneration. Secondly, approximately 90% of the product solution, which is at a temperature of approximately 80° C., must be cooled to 30° C., which is the temperature required for the preliminary stage, and this solution must then be reheated to the original saponification temperature once it has passed through this stage.

Optimum process control and avoiding or minimising waste streams are also essential in such a process both for economic reasons and for today's ecological requirements.

The object of the invention is thus to provide a process for the production of methionine or salts or precursors thereof, such as methionine nitrile or amide, wherein the process is based directly on the basic chemicals already mentioned and should also be capable of being performed on a large industrial scale without isolation of the intermediate stages. The process should be economic and, in particular, should be capable of being performed continuously, wherein it should be possible to recover the excess ammonia and ketone introduced into the process with as little loss as possible and to reuse them.

This object is achieved by the present process claimed in the claims wherein the claims may, in particular, be combined while retaining their individual advantages.

The process, which is preferably performed continuously or semi-continuously but may also be performed batchwise, comprises a total of 5 or 6 main process stages:

1.) Formation of crude MMP-cyanohydrin (CH) from MMP and HCN (preliminary stage)

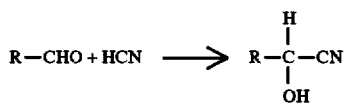

2.) Formation of crude MMP-aminonitrile from crude MMP-CH and NH₃ or NH₃/water mixtures or in a single stage from MMP, HCN and NH₃ or NH₃/water mixtures (preliminary stage)

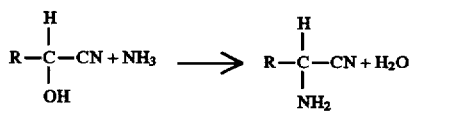

or

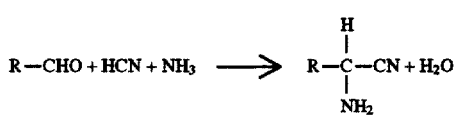

3.) Alkaline ketone-catalysed hydrolysis of crude MMP-aminonitrile (AN) to crude MMP amide

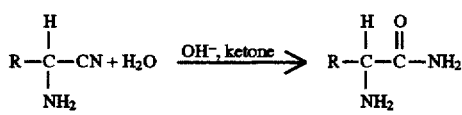

4.) Alkaline saponification of the crude product mixture from 3.) containing methionine amide (Met-AM) optionally with simultaneous partial or complete removal of ketone, NH₃ and optionally other volatile components

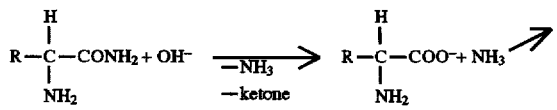

5.) Optional post-treatment of the crude methioninate solution obtained from 4.), for example by post-reaction, purification or evaporation to the desired final concentration.

6.) Ammonia/ketone purification and recycling

Re 1.) and 2.):

The formation of aminonitriles as α-amino acid precursors from aldehydes with hydrocyanic acid and ammonia (Strecker synthesis) or from initially formed cyanohydrins and ammonia (Tiemann variation) is well known and has been investigated on numerous examples (Houben-Weyl, *Methoden der Organischen Chemie*, 4th edition, 1952, volume 8, pages 274 et seq. and pages 279 et seq. and enlarged supplementary edition to the 4th edition, E5, pages 1425 et seq.). If suitable reaction conditions are selected, both reactions proceed with >90% yield.

In the present case, the Tiemann variation has the advantage that the relatively high heat of reaction of cyanohydrin formation may be collected. This enables the reaction temperature of the subsequent aminonitrile formation, which is also exothermic, to be more accurately adjusted, in particular in a continuous process.

MMP-cyanohydrin formation:

MMP-cyanohydrin is formed spontaneously from MMP and liquid or gaseous hydrocyanic acid at pH 5 to 9 and temperatures of up to 50° C., but is preferably formed at pH 5.5 to 7.5 and temperatures of 20° to 30° C.

pH is optionally maintained within the required nominal range by the addition of small quantities of base. Both organic bases such as amine compounds, for example triethylamine or pyridine, and inorganic bases such as alkali metal or alkaline earth metal hydroxides or cyanides, for example NaOH or NaCN, are suitable, particularly in the form of the aqueous solutions thereof.

The reactants should be introduced into the process in approximately equimolar quantities. An aldehyde excess should as far as possible be avoided as it results in by-products and degradation products in the subsequent reaction stages or in the end product.

A large excess of HCN should also be avoided as the hydrocyanic acid must either be driven off at a suitable stage or destroyed, which would require additional energy and complication of the process. A slight excess of HCN, in particular of up to 5%, has, however, been found to be advantageous as it enables quantitative conversion of MMP to be achieved with a selectivity of virtually ≧99.9%.

MMP-CH may be produced from MMP and gaseous or liquid hydrocyanic acid batchwise, for example in a stirred vessel, or particularly advantageously continuously in a tubular or loop reactor or in a combination of the two, as described above. Thorough mixing of the reactants with simultaneous pH and temperature monitoring are preconditions for optimum performance of this process stage.

Yields, determined by customary analytical methods such as HPLC or TLC, were 99.9%.

Aminonitrile formation:

The resultant crude MMP-cyanohydrin may be converted into crude MMP-aminonitrile by reaction with ammonia or ammonia/water mixtures in the same way as approximately equimolar mixtures of MMP and HCN or any mixture of crude MMP-cyanohydrin and MMP/HCN such as may be obtained, for example, at the cyanohydrin stage with incomplete formation of MM-CH.

While prior patent publications principally describe reactions with liquid NH₃ and MMP/HCN or MMP-CH, the advantageous use of aqueous ammonia for aminonitrile formation has more recently received greater emphasis.

DE-OS 16 43 535 describes the use of $NH_3$ excesses of 4.6 to 55 equivalents relative to MMP and $NH_3$ concentrations of above 50 wt. % under pressures above atmospheric at temperatures of up to a maximum of 60° C. and preferably of 15° to 40° C. The residence times of 4.5 to 5.5 hours are, however, excessively long, particularly for a continuous process. Moreover, the described process is accompanied by excessive by-product formation (DN and DNMA), which is also unacceptable for continuous large-scale production. Methionine yields, after acid hydrolysis of the aminonitrile, are stated to be between 97 and 99% relative to the MMP. DE-OS 20 06 979 teaches a process which proceeds under substantially identical conditions but is performed in continuously operated stirred vessels, wherein the main feature of this invention is the partial return into the reaction vessel of an aqueous phase obtained after phase separation of the crude aminonitrile, which aqueous phase is rich in $NH_3$ and still contains AN. This is stated to reduce salt formation during the subsequent acid saponification. However, the partial return of already formed product restricts the economic value of this process, in particular with regard to the acid saponification which is desired there.

DE 26 45 544 describes the use of aqueous ammonia as advantageous at $NH_3$ concentrations of 24 to 48.6 wt. %, in particular of 32 to 42 wt. %, and $NH_3$ excesses of 4 to 7 equivalents, relative to the already formed cyanohydrin introduced into the process, at temperatures of 50° to 100° C. and pressures of 1 to 10 bar. While aminonitrile may indeed be formed continuously in a tubular reactor and the reaction times are less than 30 minutes, the aminonitrile yield is at best only 96%, relative to the MMP-cyanohydrin introduced into the process. However, for a multistage process, an intermediate yield of distinctly below 100% is insufficient, from both an economic and ecological viewpoint, since it must be assumed that unreacted educt or by-products produced therefrom must be separated and disposed of in costly manner. This is unacceptable, in particular for the large scales customary for methionine production.

While yields of above 90% are indeed mentioned in all the above-stated prior patent publications, no statements are made relating to the resulting gap in the balance.

It has now been discovered according to the invention that the principal organic by-products in crude aminonitrile consist of the correspondingly substituted iminodinitrile (DN) (DN=2,2'-bis-(2-methylmercaptoethyl) iminodiacetonitrile), the dinitrile monoamide derived therefrom (DNMA) (DNMA=2,2'-bis-(2-methylmercaptoethyl) iminodiacetonitrile monoamide), together with methionine amide (AM) already formed at this stage.

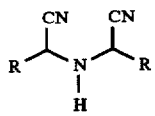
DN

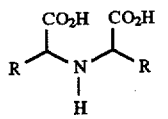
DS1

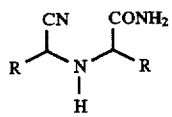
DNMA

R has the above-stated meaning.

The iminodinitrile compounds DN and DNMA, which have not hitherto been described in the literature, are partly or completely hydrolysed in the subsequent stages to yield the corresponding iminodiacid (DS1=2,2'-bis-(2-methylmercaptoethyl)iminodiacetic acid), the content of which impurity should be as low as possible in the product. Optimum performance of the aminonitrile stage, particularly with regard to those aspects important to an economic process, thus principally depends upon keeping by-product formation as low as possible while achieving a virtually quantitative yield of aminonitrile.

It has now been found that the proportion of DN+DNMA assumes an acceptably low value of ≦2 mol. % of the cyanohydrin introduced into the process, with AN yields of ≧98 mol. %, in each case relative to the reacted aldehyde, if a molar ratio of $NH_3$/CH or $NH_3$/aldehyde of at least 4:1, in particular of 5:1 to 15:1 is used and $NH_3$ concentrations of >50 wt. %, advantageously of 55 to 85 wt. %, and in particular a molar ratio of $NH_3/H_2O$ of greater than 1.5 are used at temperatures of greater than 40° C. but not greater than 80° C. and reaction times of at least 5 minutes, but not greater than 60 minutes. Dinitrile content is, in particular, raised by high temperatures or falling $NH_3$ concentrations or excesses and also by long residence times, while a low water content extends the necessary reaction time. The reaction is preferably terminated at the latest once 2% of the theoretical quantity (mol. % relative to MMP+CH) of DN+DNMA has been formed, because the proportion of DS in the finished product is otherwise too high. The reaction is generally performed within the stated limits in such a manner that the proportion of DN+DNMA is kept as low a possible. A preferred embodiment of this process stage is to use 5 to 8 equivalents of $NH_3$ with a concentration of 55 to 85 wt. %, in particular of 60 to 80 wt. %, in the temperature range of 50° to 70° C. at reaction times of 10 to 50 minutes and under the pressure which is established within the system under these conditions. Within this range, the proportion of DN+DNMA may even be reduced to <1 mol. %.

For the first time, the conditions selected here allow the process to be performed continuously at yields of above 96%, which is essential for large-scale production. A purely tubular reactor or a combination of a loop and tubular rector may be used for the process, wherein the tubular reactor should have a multiple of the residence time of the loop reactor as dinitrile formation may consequently be kept lower. The process described here is also distinguished by the fact that the ammonia or ammonia/water mixtures recovered from the subsequent recycling stages may be used instead of fresh ammonia/water.

The mixtures of crude aminonitrile/water/ammonia obtained in this manner may be used for the subsequent hydrolysis either directly or after releasing the pressure to standard pressure or to a pressure between the pressure prevailing in the system during the aminonitrile stage and standard pressure. Part of the excess $NH_3$ may be recovered at this point from the aminonitrile stage during this release of pressure.

Aminonitrile hydrolysis=methionine amide formation:

The aliphatic and cycloaliphatic ketones proposed in patents DE 26 37 204 and DE 27 53 828 for the production of amino acid amides by ketone-catalysed hydrolysis of a corresponding aminonitrile exhibit marked differences in their suitability for the hydrolysis of aminonitrile.

The greatest rate of reaction is achieved with acetone, which is the least expensive ketone and least harmful to health and thus preferred for industrial purposes.

When aminonitrile prepared as described above is hydrolysed with dilute sodium hydroxide solution in the presence of 0.2 to 2.0 equivalents of acetone at temperatures of 10° to 30° C., a product mixture is obtained which consists mainly of methionine amide, sodium methioninate, the imidazolidinone compounds IM1 and IM2, together with MMP and other components occurring in lower concentrations.

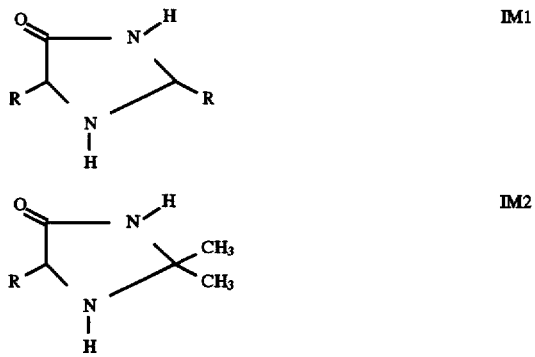

R has the above-stated meaning.

While the imidazolidinones are indeed also converted into methionine by the subsequent saponification at elevated temperatures, the IM1 and MMP contents in particular lead to losses in the final yield and may cause purity problems. According to the invention, re-formation of aldehyde and the formation of IM1 may be reduced considerably by keeping the temperature and alkali content low, so increasing the selectivity of the overall reaction sequence. A process for the production of α-amino acids as described in patent DE 27 53 829, in which the total quantity of alkali required for aminonitrile saponification, i.e. substantially 1 equivalent of hydroxide, is already added to the crude aminonitrile mixture and saponification is performed in a single stage, yields somewhat poorer results in the present case. Moreover, an increase in aldehyde content to values of up to 7 mol. % may be observed when the temperature is raised above 40° C. Aldehyde content may, however, be reduced to below 2% at temperatures of below 30° C. Since, as is known, the rate of aminonitrile hydrolysis increases sharply with ketone concentration (Commeyras et al., *Tetrahedron* 1978, 34, 2275 et seq., using the example of acetone and α-alanine nitrile), this characteristic may also be exploited for purposeful control of the reaction. An excessively large excess of ketone, such as a several times molar excess, is however undesirable for economic and product purity reasons. It has now been found that elevated reaction rates and hence very good selectivities at the AN hydrolysis stage may be achieved within a range of $H_2O$ excess with a moderate input of acetone and preferably small quantities of hydroxide. In brief, the optimum range may be placed within the following limits (relative to nitrile):

15 to 50 equivalents, preferably 20 to 30 equivalents of $H_2O$; 0.2 to 2.0 equivalents, preferably 0.3 to 1.0 equivalents of ketone; 0.1 to 1.1 equivalents, preferably 0.15 to 0.4 equivalents and in particular 0.15 to 0.3 equivalents of $OH^-$ and 1 to 7 equivalents, preferably 2 to 5 equivalents of $NH_3$ at temperatures of between 10° and 30° C., preferably of 15° to 28° C. and reaction times between 10 and 90 minutes, preferably of 20 to 60 minutes. The process described here is in particular distinguished by the fact that, instead of using ketone and water, an aqueous ketone solution obtained from a subsequent recycling stage, in particular an acetone solution, including the by-products contained therein, may be used.

As in the preceding process stages, hydrolysis of crude aminonitrile may also be performed batchwise or, preferably, continuously, the batchwise process being performed, for example, in a stirred reaction vessel. A simple reaction tube, but preferably a loop reactor, in particular a combination of loop reactor and reaction tube may be used for the continuous process. The pressure at this stage is not critical and may be selected at will in accordance with the method used, although the pressure which is established within the system in a given method is preferably used.

Amino acid hydrolysis=methioninate formation:

The solution obtained in this manner may be used directly for the subsequent saponification with alkali metal or alkaline earth metal hydroxide. To this end, the hydroxyl content which was already adjusted in the previous stage of hydrolysis is increased by the addition of further equivalents of hydroxide such that the resultant hydroxide content corresponds to a ratio of 0.95 to 1.1 equivalents, preferably 1.0 to 1.05 equivalents, relative to the MMP introduced into the process. The saponification temperature should be at least 85° C., preferably at least 90° C. but as a rule above 100° C., in particular 110° to 140° C. A temperature of 200° C. is not generally exceeded. The amide concentration is advantageously from 10 to 35 wt. %, preferably ≦30 wt. %, and in particular ≦25 wt. %, wherein a concentration of ≦25 wt. % is preferred when the saponification temperature is ≧160° C. The pressure is adjusted to the system pressure of 1 to several bar which corresponds to the selected temperature, optionally with simultaneous evaporative concentration of the reaction solution. The reaction time is at least 10 but at most 90 minutes, preferably 20 to 40 minutes in the case of alkali metal hydroxide and up to 180 minutes in the case of alkaline earth metal hydroxide.

The process according to the invention is distinguished by the fact that during and/or after saponification of the amide, the ammonia, ketone and water are drawn off together at a temperature of ≧85° C. and/or with application of a vacuum. The ketone is advantageously substantially removed from the ammonia and the ammonia transferred to the nitrile synthesis (see above). The process according to the invention may be used for all methionine syntheses in which methionine nitrile is first saponified to the amide in the presence of a ketone, in particular at a temperature of below 60° C.

According to the invention, it has been found that it is by no means necessary first to separate out the ketone present in the crude methionine amide mixture, for example as achieved according to EP B 228 938 by applying a vacuum to the resultant methionine amide solution and as proposed in DE 26 37 204 C2 (due to the low pH). Since, as has been found according to the invention, part of the ketone (2 to 10% of the quantity introduced into the process) is in any case bound as imidazolidinone (IM2 in the case of acetone) and is only liberated at the saponification stage, recirculation is also necessary here for economic and environmental reasons and the recirculation of both free and liberated ketone together during or after amide saponification is the method of choice. Preferably, no ketone is drawn off before the amide saponification stage and a second partial stream of vapours containing ketone and the consequent requirement for additional apparatus is thus avoided. Saponification may be performed batchwise in a stirred pressure reactor but is preferably performed continuously, for example in a saponification column. When the continuous method is used, it is particularly advantageous simultaneously to remove the remaining $NH_3$, including that formed in the reaction, together with any ketone still present and the steam produced in situ at the saponification temperature or the optionally additionally injected heating steam. This mixture, which escapes from the top of the column, is collected and used for recycling ammonia and ketone. The discharge from the column then contains a pale yellow amino acid salt solution containing neither ammonia nor ketone, which varies in concentration depending upon the degree of evaporation, and which has an amino acid content of 10 to 45 wt. %.

Since the crude amino acid salt solutions may still contain residues of cyanide in concentrations of several hundred ppm, these may have to destroyed. According to the invention, this is achieved by heat treatment, preferably of the directly obtained amino acid salt solutions, at above 150° C. to preferably 200° C. and residence times of up to 40 minutes, in particular of at least 10 minutes. In general, the treatment time is at least 15 minutes at $\geq 160°$ C., at least 7 minutes at $\geq 180°$ C. and at least 4 minutes at $\geq 190°$ C.

Although it is known from DE-OS 33 34 328 that residual cyanide concentrations may be destroyed by raising the temperature in an alkaline solution, DE-OS 33 34 328 relates to the destruction of bound hydrocyanic acid and acrylonitrile in crude acetonitrile, for which temperatures and pH values must be considered which are quite different from those prevailing in the amino acid reaction.

The resultant solutions have a cyanide content of only <10 ppm, relative to a 40 wt. % amino acid content. This is distinctly below the permissible limit. Thermal post-treatment may be performed successfully at any of the amino acid concentrations obtained of 10 to 45 wt. %, but preferably at 15 to 30 wt. %. It may be performed in a subsequent stage, for example in an additional reaction tube, or during the saponification itself, for example by suitably raising the temperature in the lower part of the saponification column. Cyanide saponification yields a small proportion of alkali metal or alkaline earth metal formate in the product solution, but this causes no problems since formate, in particular calcium formate, is itself used as a feedstuff additive.

Further evaporative concentration is necessary, especially if the discharge contains <40 wt. % of amino acid. This evaporation is advantageously performed at standard pressure or reduced pressure and optionally at boiling point under the mildest possible conditions, for example using a falling-film evaporator. The vapours obtained at this stage may be returned to the process at some other point.

It has also been found to be advantageous to filter the product solution, preferably through activated carbon. This may advantageously be performed in a column, especially if the process is continuous. In addition to the removal of admittedly only slight turbidity together with small quantities of by-products, a further lightening of colour occurs at this stage. This stage may be performed both before and after the possibly necessary evaporative concentration. The total yield of methionine is at least 95% in the process described here, relative to the aldehyde introduced into the process. The total quantity of detectable non-toxic iminodiacetic acid components DS1 and DS2 (N-(1-carboxy-1-methylethyl) methionine) in the solution when saponification is performed continuously is less than 1 wt. %, relative to methionine. The quality of the product solutions is in line with that used in the feedstuffs sector.

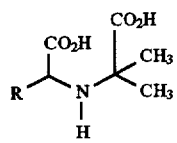

DS2

R has the above-stated meaning.

Ammonia-ketone purification and recycling:

If this process is to be economic, it is essential to reuse the excess ammonia, in particular to return it to the aminonitrile formation stage. Since one equivalent of $NH_3$ is reformed in the course of aminonitrile saponification, it is even possible, if recycling is successful, to perform the entire process without consuming any $NH_3$. In the final analysis, the nitrogen in the amino acid molecule is thus derived from the hydrocyanic acid.

It is also necessary to recycle the ketone used as completely as possible for economic reasons.

It has been found according to the invention that the ammonia used for aminonitrile formation must contain substantially no ketone, since even small quantities result in a reduced aminonitrile yield and a clearly measurable proportion of aldehyde in the crude aminonitrile and hence in losses in yield and reduced quality of the end product. The recycled ammonia should preferably contain less than 25 meq and in particular less than 10 meq of ketone, relative to the cyanohydrin and/or the aldehyde. This means that the stripped $NH_3$/ketone/water mixture cannot be recycled directly, wherein it is immaterial whether stripping is performed before, during or after amide saponification, but, as explained, the latter two methods are preferred. Indeed, $NH_3$ containing substantially no ketone must first be obtained in a yield which is as far as possible quantitative by a suitable separation method, while the ketone to be recycled may contain both water and $NH_3$.

This separation could be performed by distillation. The vapours from saponification are first collected in water in an absorption stage and the resultant solution is then fed into a distillation column at some point between the top and bottom of the column, preferably in the central to lower region of the column. If, for example, the ketone is acetone, separation to yield anhydrous ammonia containing virtually no ketone and an aqueous solution containing 5 to 30 wt. % of acetone and 0 to 5 wt. % of $NH_3$ proceeds in the column and, if the reflux ratio is suitable, this ammonia is partially or completely condensed at the top of the column and continuously discharged, while the aqueous solution containing 5 to 30 wt. % of acetone and 0 to 5 wt. % of $NH_3$ is obtained at the bottom of the column and continuously discharged from there. The column is operated at a bottom temperature of 100° to 200° C. and a pressure of 1 to 20 bar above atmospheric. The column top temperature may be from −20° to +55° C.

The pressure is preferably 5 to 18 bar above atmospheric, in particular 9 to 25 bar above atmospheric; the bottom temperature is accordingly 140° to 190° C. or 150° to 180° C. After dilution with water to establish the nominal concentration of >50 wt. % of $NH_3$, the top product may be directly returned to the aminonitrile formation stage. When this method is used, more than 95% of the acetone introduced into the process could be recovered from the bottom discharge. This solution may be used for aminonitrile hydrolysis either directly or, if desired, after filtration, optionally through an adsorbent such as for example activated carbon, instead of using fresh acetone. In this case, it is convenient first to dilute the solution with water if necessary and to make up small losses of acetone until those concentrations are obtained which, together with the crude aminonitrile mixture, result in the desired nominal concentrations of acetone and water at the aminonitrile hydrolysis stage. The required hydroxide equivalents may be introduced into the hydrolysis stage either directly by adding them to the aqueous ketone solution produced there, or by separate introduction of a suitable alkali metal hydroxide solution or alkaline earth metal hydroxide suspension. The proportions of by-product, which increase when recycling is prolonged and which principally comprise various pyridine compounds, have virtually no negative effect upon the aminonitrile hydrolysis yield in the process according to the invention. The level of by-products may, however, be kept constant at a desired level by continuously discharging small quantities, for example 1 to 10 wt. %, of the bottom solution obtained from pressure distillation and replacing them with corresponding quantities of fresh solution. The discharged amounts may either be disposed of or worked up again, in particular by-products may be eliminated and the purified substance then reused.

Description of the overall process:

The process to be performed under the conditions described above may technically be subdivided into eleven stages, as shown in the figure. These stages are preferably performed continuously but may optionally also be performed batchwise or semi-continuously. In the cyanohydrin reactor 1, a reaction between MMP and HCN is base-catalysed (KAT.) to yield MMP-cyanohydrin, which is then reacted in the aminonitrile reactor 2 with aqueous ammonia at a concentration of >50 wt. % from the absorption and mixing stage 11. The cyanohydrin reactor 1 and the aminonitrile reactor 2 may be combined into a single stage. The pressure of the resultant crude methionine nitrile/water/ammonia mixture is either reduced in a pressure reduction stage 3 and the consequently liberated $NH_3$ is removed separately (a) or b)), or the crude mixture is directly introduced into the subsequent hydrolysis stage 4 without release of pressure. In this stage 4, aminonitrile hydrolysis is performed with the assistance of a simultaneously introduced aqueous alkali metal hydroxide solution or alkaline earth hydroxide suspension (MOH) and an aqueous ketone solution, preferably in the form of the bottom product mixture obtained from the distillation 10 and optionally with the addition of fresh ketone ($\Delta$>C=O) or water ($\Delta$). The resultant solution of ketone, optionally $NH_3$, and the above-mentioned reaction products in water is introduced into the saponification reactor 5 together with a suitable alkali metal hydroxide solution or alkaline earth metal hydroxide suspension (MOH) and reacted there. The alkali metal or alkaline earth metal methioninate solution produced there is passed through a filter 7 after having passed through a heat treatment zone 6, which may also be integrated with the saponification reactor 5, and the said solution may subsequently be further concentrated in an evaporation stage 8. Alternatively or additionally, an evaporation stage 8a may be arranged downstream from the post-treatment zone 6, in which case the filter 7 has a lower liquid throughput. New adsorbent (C=activated carbon and/or filter auxiliary) and/or optionally filtration auxiliary is supplied to the filter and used adsorbent removed (C waste).

The vapours removed from the saponification reactor 5, which contain ammonia, ketone, water and by-products, are taken up in a quantity of water in an absorbtion stage 9, if desired together with the $NH_3$ (a)) from the pressure release stage 3 and the vapours from the evaporation stage 8 or 8a, such that the resultant $NH_3$ concentration is at least 20 wt. %. This solution is subsequently transferred to the distillation stage 10. The solution containing ketone obtained there as the distillation bottom product is then transferred to hydrolysis stage 4, if desired after filtration (7a) through an adsorption and/or filter auxiliary or optionally after discharge of small quantities of waste. The $NH_3$ obtained as top product is transferred to the absorption and mixing stage 11, optionally together with the $NH_3$ partial stream (b)) obtained from the pressure release stage 3. In this absorption and mixing stage 11, the $NH_3$ is adjusted to the desired concentration by the addition of water and, if necessary, small losses of $NH_3$ ($\Delta NH_3$) are replaced.

The methioninate solution produced by this process may be used directly as liquid methionine formulation for feedstuffs according to DE-OS 31 05 009 or, if desired, it may be used for the isolation of methionine or methionine derivatives using methods known from the literature.

The following examples illustrate the described process in greater detail.

EXAMPLE 1

2-Hydroxy-4-methylmercaptobutyronitrile (MMP-cyanohydrin)

(Item 1 in the figure). 250.0 kg (2,400 mol) of freshly distilled 3-(methylmercapto)propionaldehyde (MMP) and 110 ml of triethylamine were introduced at 20° C. and pH 7.0 into a 400 liter tank equipped with an anchor impeller, pH electrode, thermometer, reflux condenser, metering device and connected hydrocyanic acid evaporator. 66.0 kg (2,442 mol) of freshly evaporated, gaseous hydrocyanic acid were introduced within 7 hours with stirring at a rate such that the temperature in the tank did not exceed 30° C. The pH was maintained at 5.5 to 7.5 by the simultaneous addition of 130 ml of triethylamine. According to HPLC analysis, MMP conversion was 100%. The MMP-cyanohydrin yield was 316 kg with a cyanohydrin content of 99.6 wt. %. This cyanohydrin was used in subsequent examples.

EXAMPLE 2

(Item 1). 133.9 kg (1,285 mol) of MMP and 400 ml (=0.29 kg) of triethylamine were reacted under similar conditions to those in example 1 with 35.8 kg (1,324 mol) of liquid hydrocyanic acid within 4 hours in a 250 liter tank equipped with an anchor impeller, pH electrode, thermometer, reflux condenser, metering device and connected storage vessel containing liquid HCN. The MMP-cyanohydrin yield was 170.0 kg with a cyanohydrin content of 99.2 wt. %.

EXAMPLE 3

2-amino-4-methylmercaptobutyric acid nitrile (D,L-methionine nitrile)

(Item 2). 51.0 g (2.40 mol) of 80% aqueous ammonia were introduced at 44° C. into a 250 ml steel autoclave equipped with a stirrer, manometer, internal thermometer, feed line, pump, storage vessel and heating bath. 51.5 g (0.391 mol) of MMP-cyanohydrin were then pumped in within 2 minutes with stirring. The temperature rose to 57° C., the pressure was 13 bar above atmospheric. Stirring of the reaction mixture continued for 20 minutes at the same temperature and the mixture was then cooled in an ice bath and the pressure reduced to standard pressure. HPLC analysis of the reaction mixture indicated 99.1% of theoretical of methionine nitrile, 0.0% of theoretical of methionine amide (AM), 0.8% of theoretical of dinitrile (DN) and 0.0% of dinitrile monoamide (DNMA).

Example 4

(Item 2). Apparatus as example 3. 68.0 g (2.40 mol) of 60% aqueous ammonia were introduced into the autoclave at 50° C. 53.6 g (0.407 mol) of MMP-cyanohydrin were then pumped in within 2 minutes with stirring. The temperature rose to 58° C., the pressure was 7 bar above atmospheric. Stirring of the reaction mixture was continued for 10 minutes at the same temperature and the mixture was then cooled in an ice bath and depressurised to standard pressure. HPLC analysis of the reaction mixture indicated 99.0% of theoretical of methionine nitrile, 0.0% of theoretical of AM, 0.9% of theoretical of dinitrile (DN) and 0.0% of theoretical of DNMA.

EXAMPLE 5

(comparison)

102.0 g (2.40 mol) of 40% aqueous ammonia were reacted with 55.2 g (0.419 mol) of MMP-cyanohydrin in a similar manner to example 3. HPLC analysis indicated 98.0% of theoretical of methionine nitrile, 0.3% of theoretical of methionine amide, 1.4% of theoretical of DN and 0.3% of theoretical of dinitrile monoamide (DNMA).

EXAMPLE 6

(comparison)

122.4 g (1.80 mol) of 25% aqueous ammonia were reacted with 41.1 g (0.312 mol) of MMP-cyanohydrin in a similar manner to example 3. HPLC analysis indicated 95.8% of theoretical of methionine nitrile, 1.6% of theoretical of methionine amide, 1.6% of theoretical of DN and 1.0% of theoretical of DNMA.

EXAMPLE 7

(comparison)

(Item 2 without item 1). In the apparatus described in example 3, 122.4 g (1.80 mol) of 25% aqueous ammonia were introduced into the autoclave at 42° C. A solution of 8.5 g (0.314 mol) of HCN in 31.7 g (0.304 mol) of MMP was then pumped in within 4 minutes with stirring. The temperature rose to 53° C., the pressure was 1 bar above atmospheric. Stirring of the reaction mixture was continued for a further 10 minutes at the same temperature and the mixture was then cooled in an ice bath and depressurised to standard pressure. HPLC analysis of the reaction mixture indicated 91.8% of theoretical of methionine nitrile, 1.8% of theoretical of methionine amide, 1.7% of theoretical of DN, 1.2% of theoretical of DNMA.

EXAMPLE 8

(Item 2 without item 1). 51.0 g (1.80 mol) of 60% aqueous ammonia were introduced into the autoclave at 32° C. in a similar manner to example 7. A solution of 8.5 g (0.314 mol) of HCN in 32.2 g (0.309 mol) of MMP was then pumped in within 0.7 min with stirring. The temperature rose to 54° C., the pressure was 5 bar above atmospheric. Stirring of the reaction mixture was continued at the same temperature for 10 minutes and the mixture was then cooled in an ice bath and depressurised to standard pressure. HPLC analysis of the reaction mixture indicated 97.6% of theoretical of methionine nitrile, 0% of theoretical of methionine amide, 1.5% of theoretical of DN, 0.5% of DNMA, 0.2% of theoretical of MMP and 0.2% of theoretical of CH.

EXAMPLE 9

(Item 2). 68.0 g (2.40 mol) of 60% aqueous ammonia were introduced at 31° C. into a 250 ml steel autoclave equipped with a stirrer, manometer, internal thermometer, feed line, sampling device, pump, storage vessel and heating bath. 52.9 g (0.402 mol) of MMP-cyanohydrin were then pumped in within 2 minutes with stirring. The temperature rose to 39° C. Stirring of the reaction mixture was continued at 40° C. for 60 minutes and samples were taken for HPLC analysis after 10 and 60 minutes. The following yields were obtained:

|  | Methionine nitrile | MMP | MMP-CH | DN |
|---|---|---|---|---|
| after 10 min: | 63.5 | 2.4 | 34.0 | 0.1% of theoretical |
| after 60 min: | 97.4 | 0.6 | 0.4 | 1.6% of theoretical |

EXAMPLE 10

(comparison)

(Item 2). 116.3 g (2.60 mol) of 38% aqueous ammonia were introduced into the autoclave at 68° C. in a similar manner to example 3. 54.3 g (0.412 mol) of MMP-cyanohydrin were then pumped in with stirring within 1.6 minutes. The temperature rose to 80° C., the pressure was 5 bar above atmospheric. Stirring of the reaction mixture was continued at the same temperature for 10 minutes and the mixture was then cooled in an ice bath and depressurised to standard pressure. HPLC analysis of the reaction mixture indicated 93.0% of theoretical of methionine nitrile, 0.45% of theoretical of methionine amide, 1.35% of theoretical of MMP, 4.60% of theoretical of DN and 0.55% of DNMA.

EXAMPLE 11

(comparison)

(Item 2). 68.0 g (2.40 mol) of 60% aqueous ammonia and 4.7 g (0.08 mol) of acetone were introduced into the autoclave at 44° C. in a similar manner to example 3.53.7 g (0.408 mol) of MMP-cyanohydrin were then pumped in within 2 minutes with stirring. The temperature rose to 56° C., the pressure was 6 bar above atmospheric. Stirring of the reaction mixture continued at the same temperature for 10 minutes and the mixture was then cooled in an ice bath and depressurised to standard pressure. HPLC analysis of the reaction mixture indicated 91.6% of theoretical of methionine nitrile and 8.4 of theoretical of MMP.

EXAMPLE 12

(Item 2). For the continuous process, 2.55 kg (89.8 mol) per hour of aqueous 60% ammonia preheated to 40° C. and 1.923 kg (14.60 mol) per hour of MMP-cyanohydrin were both simultaneously introduced into a heatable reaction tube preceded by a mixing section and equipped with an internal temperature measuring device, sampling device and connected MM-CH feed line with storage vessel and $NH_3$ feed line with storage vessel and interposed heat exchanger. The reaction temperature was adjusted to 55° C. at the reaction tube inlet and 56° C. at the tube outlet and pressure was 7.8 bar above atmospheric and the residence time 17.3 minutes. HPLC analysis of samples taken at the tube outlet indicated 97.2% of theoretical of methionine nitrile, 0.3% of theoretical of methionine amide, 0.5% of theoretical of MMP and 1.8% of theoretical of DN.

EXAMPLE 13

(Item 2). 2.45 kg (86.3 mol) per hour of 60% aqueous ammonia were reacted with 2.371 kg (18.0 mol) per hour of MMP-cyanohydrin in a similar manner to example 12 at a residence time of 21.8 minutes. HPLC analysis indicated 95.2% of theoretical of methionine nitrile, 0.0% of theoretical of methionine amide, 1.7% of theoretical of DN, 0.7% of theoretical of MMP-CM and 0.4% of theoretical of MMP.

EXAMPLE 14

(Item 2). 2.07 kg (97.2 mol) per hour of aqueous 80% ammonia preheated to 53° C. and 1.917 kg (14.56 mol) per hour of MMP-cyanohydrin were simultaneously introduced in a similar manner to example 12. The reaction temperature was adjusted to 57° C. at the tube inlet and 56° C. at the tube outlet, the pressure was 14.4 bar above atmospheric and the residence time was 24.5 minutes. HPLC analysis of samples taken at the tube outlet indicated 98.2% of theoretical of methionine nitrile, 0.0% of theoretical of methionine amide, 1.3% of theoretical of DN and 0.4% of theoretical of MMP.

EXAMPLE 15

D,L-methionine amide solution (Items 2, 3 and 4). 50.0 g (1.76 mol) of 60% aqueous ammonia were introduced at 45° C. into a 250 ml steel autoclave equipped with a stirrer, manometer, internal thermometer, feed line, pump, storage vessel and heating bath. 37.25 g (0.283 mol) of MMP-cyanohydrin were then pumped in within 1.5 minutes with stirring. The temperature rose to 54° C., the pressure was 7 bar above atmospheric. Stirring of the reaction mixture was continued for 10 minutes at the same temperature and the pressure was then released to standard pressure with simultaneous cooling.

A solution of 2.5 g (0.063 mol) of NaOH and 8.8 g (0.152 mol) of acetone in 110 g (6.11 mol) of water was then pumped into the mixture, which was at a temperature of 15° C., while the mixture was cooled with water, and the temperature rose to 27° C. Stirring of the reaction mixture was continued for 30 minutes at 25° C. and the mixture was then immediately analysed. The clear, pale yellow solution (201.1 g) was of the following composition:

| | |
|---|---|
| 19.93 wt. % of methionine amide | 95.60% of theoretical |
| 0.38 wt. % of methionine | 1.80% of theoretical |
| 0.06 wt. % of IM1 | 0.35% of theoretical |
| 0.46 wt. % of IM2 | 1.70% of theoretical |
| 0.05 wt. % of MMP | 0.35% of theoretical |

EXAMPLE 16

(Items 2, 3 and 4). 51.0 g (1.80 mol) of 60% aqueous ammonia were introduced into the autoclave at 45° C. in a similar manner to example 15. 42.0 g (0.319 mol) of MMP-cyanohydrin were then pumped in within 1.5 minutes with stirring. The temperature rose to 54° C., the pressure was 7 bar above atmospheric. Stirring of the reaction mixture was continued at the same temperature for 10 minutes and the pressure was then released to standard pressure with simultaneous cooling.

A solution of 12.2 g (0.31 mol) of NaOH and 8.8 g (0.152 mol) of acetone in 113 g (6.27 mol) of water was pumped with simultaneous cooling into the mixture, which was at a temperature of 15° C., and the temperature rose to 27° C. Stirring of the reaction mixture was continued at 25° C. for 30 minutes and the mixture was then immediately analysed. The cloudy, pale yellow solution (208.3 g) was of the following composition:

| | |
|---|---|
| 18.8 wt. % of methionine amide | 82.8% of theoretical |
| 2.8 wt. % of methionine | 12.2% of theoretical |
| 0.0 wt. % of IM1 | 0% of theoretical |
| 0.77 wt. % of IM2 | 2.7% of theoretical |
| 0.17 wt. % of MMP | 1.1% of theoretical |

EXAMPLE 17

An MMP-CH feed line which is connected with a storage vessel and an ammonia feed line which is connected with an absorption and mixing stage (item 11) via a heat exchanger are connected via a mixing section to a heatable flow tube equipped with an internal temperature measuring device (item 2). The flow tube is connected via an automatic pressure maintaining valve to a stirred depressurising vessel (item 3), the gas space of which is connected with an absorption stage (item 9) via a line, while the bottom discharge of the depressurising vessel leads to the hydrolysis stage (item 4) via a pump. The hydrolysis stage may be thermostatically controlled and consists of a loop reactor with circulating pump and a flow tube downstream therefrom. The loop reactor is connected at its input end to the storage vessel for aqueous acetone/NaOH solution via a feed line and pump and the flow tube is connected to a receiver via a pressure control device. The absorption stage (item 9) is an $NH_3$ absorption system consisting of a bottom container with circulating pump and quencher and a bubble-cap column mounted thereon.

The top of the column is supplied from a fresh water tank via a supply line and pump. The bottom discharge opens into a receiver.

The average hourly amounts introduced into the flow tube (item 2) were 1.925 kg (14.61 mol) of MMP-cyanohydrin and 2.55 kg (89.8 mol) of 60% ammonia from item 11 preheated to 40° C., both amounts being flow controlled. The reaction temperature was adjusted to 55° C. at the tube inlet and 56° C. at the tube outlet, the pressure was 7.8 bar above atmospheric and the residence time was 23 minutes. The pressure in the depressurising vessel (item 3) was 1.2 bar above atmospheric, the temperature was 35° C. The level of crude amino nitrile in the depressurising vessel was held constant by a constant supply to the hydrolysis stage (item 4).

In the loop reactor of the hydrolysis stage (item 4), 6.40 kg per hour of an aqueous solution containing 7.25 wt. % (0.464 kg, 7.99 mol) of recycled acetone, 2.0 wt. % (0.128 kg, 3.2 mol) of NaOH and 3.3 wt. % (0.211 kg, 12.4 mol) of $NH_3$ were pumped in from a storage vessel in addition to the crude aminonitrile mixture from the pressure release stage (item 3). The temperature in the loop reactor was 27° C. and 26° C. in the reaction tube and the total residence time was 50 minutes.

The temperature in the $NH_3$ absorption stage (item 9) was maintained at 22° C. and the pressure at 1.2 bar above atmospheric. An average of 10.58 kg per hour of a pale yellow, aqueous solution of the following composition was obtained in the discharge of the hydrolysis stage (item 4):

| | |
|---|---|
| 19.19 wt. % of methionine amide | 93.8% of theoretical |
| 0.31 wt. % of methionine | 1.5% of theoretical |
| 0.38 wt. % of IM2 | 1.5% of theoretical |
| 0.26 wt. % of MMP | 1.8% of theoretical |

EXAMPLE 18

D,L-sodium methioninate solution (Items 2, 3, 4, 5 and 6). A feed line with pump and storage vessel are connected to a 250 ml steel autoclave equipped with a stirrer, manometer, internal thermometer and heating bath.

38.3 g (1.80 mol) of 80% aqueous ammonia were introduced into the autoclave at 42° C. and 37.80 g (0.287 mol) of MMP-cyanohydrin were then pumped in within 1.5 minutes with stirring. Stirring of the reaction mixture was continued for 20 minutes at 56° C. and the mixture was then depressurised from 11 bar above atmospheric to standard pressure and simultaneously cooled. 14.4 g (0.84 mol) of $NH_3$ were recovered. A solution of 2.5 g (0.063 mol) of NaOH and 8.8 g (0.152 mol) of acetone in 122 g (6.77 mol) of water was pumped with simultaneous cooling into the mixture, which was at a temperature of 20° C., and the reaction temperature rose to 25° C. Stirring was continued for a further 35 minutes at the same temperature. 18.6 g (0.233 mol) of 50% sodium hydroxide solution were then pumped in and the reaction mixture stirred for 30 minutes at standard pressure and 100° to 105° C. Stirring was then continued for 30 minutes at 160° C. and 15 bar above atmospheric. The resultant pale yellow solution was filtered and concentrated by evaporation at standard pressure. 102.3 g of a yellow solution of the following composition were obtained:

| 40.15 wt. % of methionine | 95.9% of theoretical |
|---|---|
| Trace DS1 | |
| 0.42 wt. % of DS2 | 0.64% of theoretical |
| <10 ppm of cyanide. | |

EXAMPLE 19

51.0 g (1.80 mol) of 60% aqueous ammonia were introduced into the autoclave at 44° C. in a similar manner to example 18 and 38.5 g (0.292 mol) of MMP-cyanohydrin were then pumped in within 1.5 minutes with stirring. The reaction mixture was stirred for a further 11 minutes at 55° C. and depressurised from 6 bar above atmospheric to standard pressure with simultaneous cooling. 12.3 g of $NH_3$ were recovered. A solution of 2.5 g (0.063 mol) of NaOH and 8.8 g (0.152 mol) of acetone in 115 g (6.38 mol) of water was pumped with simultaneous cooling into the mixture, which was at a temperature of 20° C., and the reaction temperature rose to 25° C. Stirring was continued at the same temperature for a further 32 minutes. 18.6 g (0.233 mol) of 50% sodium hydroxide solution were then pumped in and stirring was continued for a further 45 minutes at 160° C. and 21 bar above atmospheric. The resultant pale yellow solution was filtered and concentrated by evaporation at standard pressure. After cooling to room temperature, 100.8 g of a yellow solution of the following composition were obtained:

| 41.7 wt. % of methionine | 96.5% of theoretical |
|---|---|
| <0.04 wt. % of DS1 | <0.01% of theoretical |
| 0.42 wt. % of DS2 | 0.6% of theoretical |
| <10 ppm of cyanide. | |

EXAMPLE 20

A sodium methionate solution was prepared in a similar manner to example 19 from 50.0 g (1.76 mol) of 60% ammonia, 39.3 g (0.298 mol) of MMP-cyanohydrin, a solution of 2.5 g (0.063 mol) of NaOH and 3.6 g (0.062 mol) of acetone in 79.6 g (4.42 mol) of water and 18.8 g (0.235 mol) of a 50% sodium hydroxide solution. 101.8 g of a light brown solution of the following composition were obtained:

| 41.2 wt. % of methionine | 94.3% of theoretical |
|---|---|
| 0.20 wt. % of DS1 | 0.5% of theoretical |
| 0.66 wt. % of DS2 | 1.0% of theoretical |

EXAMPLE 21

(comparison)

122.2 g (1.80 mol) of 25% aqueous ammonia were introduced into the autoclave at 50° C. in a similar manner to example 18 and 39.4 g (0.299 mol) of MMP-cyanohydrin were then pumped in within 1.5 minutes with stirring. Stirring of the reaction mixture was continued for a further 10 minutes at 55° C. and 2 bar above atmospheric and the mixture was then cooled. 6.2 g (0.062 mol) of 40% sodium hydroxide solution and 3.6 g (0.062 mol) of acetone were then pumped into unpressurised mixture which was at a temperature of 20° C., wherein the reaction temperature rose to 36° C. The mixture was then stirred for a further 60 minutes at 33° C. 19.1 g (0.239 mol) of 50% sodium hydroxide solution were then pumped in and stirring was continued for 45 minutes at 160° C. and 21 bar above atmospheric. The resultant solution was filtered and concentrated by evaporation at standard pressure. After cooling to room temperature, 104.2 g of a reddish-brown solution of the following composition were obtained:

| 39.65 wt. % of methionine | 92.6% of theoretical |
|---|---|
| 0.59 wt. % DS1 | 1.5% of theoretical |
| 0.56 wt. % of DS2 | 0.8% of theoretical. |

EXAMPLE 22

An MMP-CH feed line which is connected to a storage vessel and an ammonia feed line which is connected to an absorption and mixing stage (item 11) via a heat exchanger are connected via an upstream mixing section to a heatable flow tube equipped with an internal temperature measuring device (item 2). The flow tube (item 2) is directly connected with a thermostatically controllable hydrolysis stage (item 4) and consists of a loop reactor with circulating pump followed by a flow tube. The loop reactor is connected at its input end to a storage vessel for aqueous acetone/NaOH solution via a feed line and pump and at its output end to a saponification reactor (item 5) via the flow tube and pressure regulating device. The saponification reactor consists of a bubble-cap column, the uppermost tray of which is connected with a storage container for sodium hydroxide solution via a feed line and pump, while the top of the column is connected to an absorption stage (item 9) via a pressure maintaining device. The column bottom comprises a circulation evaporator. The level-controlled bottom discharge of the saponification reactor is linked to a post-treatment zone (item 6) via an intermediate container and pump. The post-treatment zone consists of a preheater and a residence time section downstream therefrom and is directly connected to a filter (item 7) via a thermostatically controllable line and pressure maintaining device. The filter is a fine filter which discharges into a stage in which evaporative concentration takes place (item 8). This evaporative concentration stage is an evaporation system consisting of a falling-film evaporator, a condenser downstream therefrom and a product collecting vessel. The absorption stage (item 9) serves to absorb $NH_3$ and comprises a bottom container with circulating pump and quencher and a bubble-cap column mounted thereon. The top of the column is supplied from a fresh water container via a feed line and pump while the line carrying the vapours from the top of the saponification column (item 5) and the condensate line of the evaporation stage (item 8) open into the quencher. The bottom discharge of the absorption stage (item 9) is connected via a pump to a distillation unit (item 10) which acts as a pressure distillation system for the continuous separation of $NH_3$ from the input mixture and is designed as a bubble-cap column. Input from the absorption stage (item 9) proceeds in the centre of the column.

The bottom part consists of a circulation evaporator provided with a level-controlled, coolable discharge and connected via this discharge with a receiving vessel which in turn is connected to the storage container for the aqueous acetone/NaOH solution.

The top part consists of a condenser with attached receiver connected by a flow control to the absorption and mixing stage (item 11), which consists of a constant-pressure stirred tank, which is additionally equipped with means for supplying liquid ammonia and fresh water.

An average of 1.774 kg (13.47 mol) per hour of MMP-cyanohydrin and 2.55 kg (89.8 mol) per hour of ammonia preheated to 40° C. from item 11 were introduced into the flow tube under flow control. The reaction temperature was adjusted to 55° C. at the tube inlet and 50° C. at the tube outlet, pressure was 7.8 bar above atmospheric and the residence time was 23 minutes. 6.0 kg per hour of an aqueous solution containing 7.25 wt. % (7.50 mol) of acetone and 2.0 wt. % (3.00 mol) of NaOH were pumped into the loop reactor (item 4) from a storage vessel. The temperature was 29° C. in the loop reactor and 25° C. in the reaction tube and the total residence time was 50 minutes. 0.86 kg (10.75 mol) per hour of 50% aqueous sodium hydroxide solution were pumped into the saponification reactor (item 5). The temperature was 132° C. at the bottom and 118° C. at the top of the column, the pressure was 1.7 bar above atmospheric and the total residence time was 26 minutes.

The temperature in the vapour absorption stage (item 9) was maintained at 19° to 22° C. and the pressure at 0.3 to 1.0 bar above atmospheric by cooling and pumping in an average of 1 liter of water per hour. 5.5 to 6.5 liters of solution per hour were fed from the vapour absorption stage into the pressure distillation column. The temperature was 161° to 163° C. at the bottom and 28° to 29° C. at the top, the pressure was 10 bar above atmospheric and the reflux ratio was adjusted to 0.5 to 0.6. An average of 4.0 kg per hour of an aqueous solution containing 11 to 12 wt. % of acetone and 2.0 to 2.7 wt. % of $NH_3$ were collected in the bottom discharge receiver. Water, acetone and sodium hydroxide solution were added to this solution until the total concentration was equal to the above-mentioned nominal concentration and the resultant solution was then introduced into the storage vessel for the hydrolysis stage (item 4). 2.5 liters of condensed ammonia per hour were introduced into item 11 from the column top receiver, together with 1 liter of fresh water per hour. Slight losses were made good from time to time by introducing fresh $NH_3$ and fresh water. The temperature in the post-reactor (item 6) was 180° C., the pressure was 12 bar above atmospheric and the residence time was 20 minutes. After release of pressure to standard pressure and cooling to 90° to 95° C., the solution was filtered (item 7) and then concentrated in the falling-film evaporator (item 8) at 135° to 140° C./0.5 bar. An average of 4.69 kg per hour of a yellow aqueous sodium methioninate solution of the following composition were obtained in the discharge from the evaporation stage (item 8):

| | |
|---|---|
| 40.7 wt. % of methionine | 95.0% of theoretical |
| 0.15 wt. % of DS1 | 0.4% of theoretical |
| 0.18 wt. % of DS2 | 0.3% of theoretical |
| 6.74 wt. % of sodium | |
| <5 ppm of cyanide. | |

EXAMPLE 23

The same method is used as in example 22, with a depressurising stage (item 3) interposed between the flow tube (item 2) and the hydrolysis stage (item 4).

The depressurising stage (item 3) is a stirred depressurising vessel, the gas space of which is connected to the absorption stage (item 9), while the bottom discharge is connected to the hydrolysis stage (item 4) via a pump.

The filter (item 7) consists of two activated carbon filter columns arranged in series through which the liquid flows from the bottom upwards such that the discharge from the second column enters the evaporation stage (item 8).

An average of 1.931 kg (14.66 mol) of MMP-cyanohydrin and 2.61 kg (92.0 mol) of 60% ammonia preheated to 40° C. (from item 11) were introduced into the flow tube (item 2), each under flow control. The reaction temperature was adjusted to 55° C. at the tube inlet and 56° C. at the tube outlet, the pressure was 7.8 bar above atmospheric and the residence time 23 minutes. The reaction mixture was depressurised to 0.9 to 1.2 bar above atmospheric at 30° C. in the depressurisation stage (item 3) and pumped into the loop reactor (item 4) into which 6.0 kg of an aqueous solution containing 7.25 wt. % (7.5 mol) of acetone and 2.0 wt. % (3.0 mol) of NaOH were pumped simultaneously from a storage vessel. The temperature was 26° C. in the loop and 25° C. in the reaction tube and the overall residence time was 50 minutes.

0.92 kg (11.50 mol) per hour of 50% sodium hydroxide solution were pumped into the saponification reactor (item 5). The temperature was 135° C. at the bottom and 122° C. at the top of the column, the pressure was 1.7 bar above atmospheric and the total residence time 26 minutes.

The temperature in the vapour absorption stage (item 9) was maintained at 21° to 27° C. and the pressure at 0.9 to 1.2 bar above atmospheric by cooling and pumping in an average of 1.8 l of water. 5.5 to 6.5 liters of solution per hour were introduced from item 9 into the pressure distillation column. The temperature was 160° to 161° C. at the bottom and 28° to 29° C. at the top, the pressure was 10 bar above atmospheric and the reflux ratio was adjusted to 0.5 to 0.6. An average of 4.0 kg of an aqueous solution containing 10 to 12 wt. % of acetone and 2.0 to 3.0 wt. % of $NH_3$ were collected in the receiver of the bottom discharge per hour. Water, acetone and sodium hydroxide solution were added to this solution until the total concentration was equal to the above-mentioned nominal concentration and the resultant solution was then introduced into the hydrolysis stage storage vessel (item 4). 2.5 liters per hour of condensed ammonia from the receiver for the top part of the distillation column were introduced into item 11 together with 1 liter of fresh water per hour. Slight losses were made good from time to time by the appropriate addition of fresh $NH_3$ and fresh water. The temperature in the post-reactor (item 6) was 180° C., the pressure was 12 bar above atmospheric and the residence time was 20 minutes. After release of pressure to standard pressure and cooling to 80° C., the solution was passed at this temperature over a total of 13 kg of activated carbon (item 7) and then concentrated in the falling-film evaporator (item 8) at 135° to 140° C./0.5 bar. An average of 4.945 kg per hour of a light yellow, aqueous sodium methioninate solution of the following composition were obtained in the discharge from item 8:

| 42.16 wt. % of methionine | 95.3% of theoretical |
|---|---|
| 0.18 wt. % of DS1 | 0.4% of theoretical |
| 0.20 wt. % of DS2 | 0.3% of theoretical |
| 6.74 wt. % of sodium | |
| <2 ppm of cyanide. | |

EXAMPLE 24

Apparatus as described in example 23. An average of 1.978 kg (15.02 mol) per hour of MMP-cyanohydrin and 2.01 kg (94.4 mol) per hour of 80% ammonia preheated to 40° C. (from item 11) were introduced under flow control into the flow tube (item 2). The reaction temperature was adjusted to 58° C. at the tube inlet and 56° C. at the tube outlet, the pressure was 14.2 bar above atmospheric and the residence time was 24.6 minutes. The reaction mixture was depressurised to 0.9 to 1.0 bar above atmospheric at 30° C. in the depressurising stage (item 3) and pumped into the loop reactor (item 4), into which 6.7 kg per hour of an aqueous solution containing 6.55 wt. % (7.56 mol) of acetone and 1.8 wt. % (3.02 mol) of NaOH were pumped simultaneously from a storage vessel. The temperature in the loop was 26° C. and 25° C. in the reaction tube and the total residence time was 50 minutes.

0.96 kg (11.98 mol) per hour of 50% sodium hydroxide solution were pumped into the saponification reactor (item 5). The temperature was 133° C. at the bottom and 118° C. at the top of the column, the pressure was 1.7 bar above atmospheric and the total residence time was 26 minutes.

By cooling and pumping an average of 2.4 liters of water per hour into the vapour absorption stage (item 9), the temperature at that stage was maintained at 19° to 22° C. and the pressure at 0.9 to 1.0 bar above atmospheric. 5.5 to 6.5 liters per hour of solution were introduced from item 9 into the pressure distillation column. The temperature was 159° to 161° C. at the bottom and 28° to 29° C. at the top, the pressure was 10 bar above atmospheric and the reflux ratio was adjusted to 0.4 to 0.5. An average of 4.0 kg per hour of an aqueous solution containing 10 to 12 wt. % of acetone and 2.0 to 3.0 wt. % of NH$_3$ was collected in the bottom discharge receiver. Water, acetone and sodium hydroxide solution were added to this aqueous solution until the total concentration obtained was equal to the above-mentioned nominal concentration and the resultant solution was then introduced into the storage container for the hydrolysis stage (item 4). 2.5 liters per hour of condensed ammonia were introduced into item 11 from the receiver for the top of the distillation column, together with 0.4 liters per hour of fresh water. Slight losses were made good from time to time by the appropriate addition of fresh NH$_3$ and fresh water. The temperature in the post-reactor (item 6) was 180° C., the pressure was 12 bar above atmospheric and the residence time was 20 minutes. After releasing the pressure to standard pressure and cooling to 80° C., the solution was passed at this temperature over a total of 13 kg of activated carbon (item 7) and then concentrated in the falling-film evaporator (item 8) at 135° to 140° C./0.5 bar. An average of 4.87 kg per hour of a pale yellow, aqueous sodium methioninate solution of the following composition were obtained in the discharge from item 8:

| 44.25 wt. % of methionine | 96.2% of theoretical |
|---|---|
| 0.14 wt. % of DS1 | 0.3% of theoretical |
| 0.18 wt. % of DS2 | 0.2% of theoretical |
| 7.08 wt. % of sodium | |
| <5 ppm of cyanide. | |

EXAMPLE 25

Calcium methioninate solution (Item 5). 13.1 g (0.170 g) of Ca(OH)$_2$ (96%) were added with stirring to a solution of 50.0 g (0.330 mol) of methionine amide (97.8%) in 223.2 g of water in a 350 ml steel autoclave equipped with a stirrer, manometer, internal thermometer and heating bath and, once the reaction mixture had been heated to 130° C., it was stirred at this temperature and 2 bar above atmospheric for 120 minutes. The reaction mixture was depressurised to standard pressure and simultaneously cooled. 286.2 g of yellowish filtrate containing 17.06 wt. % of methionine, 99.2% of theoretical, and 0.08 wt. % of methionine amide, 0.5% of theoretical, were obtained.

We claim:

1. In process for the production of methionine or a salt thereof by hydrolysis of methionine nitrile to methionine amide in the presence of a ketone, followed by saponification with a base to form a crude methionine product mixture wherein the improvement comprises simultaneously drawing off ammonia, ketone and water at a temperature of ≧85° C. by application of a vacuum or vacuum or by distillation either during and/or after saponification of the amide.

2. The process according to claim 1, characterised by forming the methionine nitrile by the reaction of methylmercaptopropionaldehyde (MMP) with hydrocyanic acid and ammonia or by reaction of the corresponding cyanohydrin (CH) with ammonia or by the reaction of any mixture of MMP/hydrocyanic acid and the corresponding cyanohydrin with ammonia.

3. The process according to claim 1 or 2, characterised in that the ketone is separated from the ammonia.

4. The process according to claim 3, wherein the separated ammonia contains substantially no ketone and is transferred to the nitrile synthesis.

5. In process for the production of methionine amide, methionine or a salt thereof by the reaction of methylmercaptopropionaldehyde (MMP) with hydrocyanic acid and ammonia or of the corresponding cyanohydrin (CH) with ammonia or a mixture of MMP, CH, hydrocyanic acid and ammonia to form methionine nitrile, followed by hydrolysis of the nitrile in the presence of a ketone to the amide, optionally followed by saponification of the amide, separation of the excess ammonia and at least partial return of the separated excess ammonia to the nitrile synthesis stage, wherein the improvement comprises substantially removing the ketone from the ammonia before recycling separated ammonia to the nitrile synthesis stage.

6. The process according to claim 5, wherein the recycled ammonia contains less than 25 meq of the cyanohydrin and/or aldehyde.

7. In process for the separation of ammonia from an ammonia/ketone/water mixture wherein the improvement comprises feeding the mixture into a central region or a lower half of a column, maintaining the column at a pressure of 1 to 20 bar above atmospheric and the bottom temperature at 100° to 200° C. and drawing off the ketone, water and optionally small quantities of ammonia from the sump.

8. The process according to claim 7, wherein the pressure is 5 to 18 bar above atmospheric and the temperature is 140° to 190° C.

9. The process according to claim 7, wherein the mixture has been separated after or during saponification of an amino acid amide and/or an amino acid nitrile.

10. The process according to claim 8 characterised in that a pressure of 9 to 15 bar above atmospheric and a temperature of 150° to 180° C. are used.

11. The process according to claim 1 wherein the methionine nitrile is formed by the reaction of methylmercaptopropionaldehyde (MMP) with hydrocyanic acid and ammonia and/or the reaction of MMP-cyanohydrin with ammonia to form methionine nitrile and the methionine amide is formed by the hydrolysis of the nitrile, wherein the ammonia and cyanohydrin or ammonia and MMP are introduced in a molar ratio of at least 4:1, and the ammonia is present at a concentration of above 50 wt. %, the reaction temperatures are from 40° C. to 80° C. and the reaction time is from 5 to 60 minutes.

12. The process according to claim 11, wherein the reaction is terminated when at the latest when 2% of theoretical of 2,2'-bis-(2-methylmercaptoethyl)-iminodiacetonitrile and/or 2,2'-bis-(2-methylmercaptoethyl)iminodiacetonitrile monoamide have been formed.

13. The process of claim 11, wherein the process is continuous.

14. The process of claim 11, wherein the improvement further comprises saponifying the amide at a concentration less than or equal to 25 wt. % and at a temperature of 160° C. or higher to form methionine or its salts.

15. The process of claim 14, wherein the improvement further comprises saponifying the amide at a temperature that does not exceed 200° C.

16. In process for the production of methionine amide, methionine or a salt thereof by the hydrolysis of methionine nitrile to methionine amide in the presence of a ketone, optionally followed by saponification with a base, wherein the improvement comprises hydrolyzing the nitrile in the presence of 15 to 50 eq of $H_2O$, 0.2 to 2 eq of ketone, 0.1 to 1.1 eq of hydroxide and 1 to 7 eq of $NH_3$, in each case relative to the nitrile, and at a temperature of 10° to 30° C. and a reaction time of 10 to 90 minutes.

17. In a process for the production of an amino acid or a salt thereof by the reaction of an appropriate aldehyde with hydrocyanic acid and ammonia or by the reaction of a corresponding aldehyde with hydrocyanic acid followed by a reaction with ammonia to the nitrile of the amino acid, hydrolysis of the nitrile of the amino acid to the amide of the amino acid and subsequent saponification with a base, wherein the improvement comprises saponifying at a temperature of above 150° C. for up to 40 minutes until the cyanide content of the solution has been reduced to below 10 ppm, relative to a 40 wt. % amino acid solution.

18. The process according to claim 17, wherein the heating is performed at $\geq 160°$ C. for at least 15 minutes.

* * * * *